United States Patent
Arnitz

(10) Patent No.: US 10,363,361 B2
(45) Date of Patent: Jul. 30, 2019

(54) DEVICE FOR THE DOSED DISPENSING OF A FLUIDIC MEDIUM

(75) Inventor: Theo Arnitz, Waghaeusel (DE)

(73) Assignee: Roche Diabetes Care, Inc., Indianapolis, IN (US)

( * ) Notice: Subject to any disclaimer, the term of this patent is extended or adjusted under 35 U.S.C. 154(b) by 509 days.

(21) Appl. No.: 13/524,760

(22) Filed: Jun. 15, 2012

(65) Prior Publication Data

US 2013/0158501 A1 Jun. 20, 2013

(30) Foreign Application Priority Data

Jun. 16, 2011 (EP) .................................... 11170216

(51) Int. Cl.
*A61M 5/172* (2006.01)
*A61M 5/142* (2006.01)
*A61M 5/145* (2006.01)

(52) U.S. Cl.
CPC .......... *A61M 5/172* (2013.01); *A61M 5/1454* (2013.01); *A61M 5/14232* (2013.01)

(58) Field of Classification Search
CPC ................ A61M 5/172; A61M 5/1685; A61M 5/14232; A61M 5/1454; A61M 39/28
USPC .................................... 604/65, 181, 187, 218
See application file for complete search history.

(56) References Cited

U.S. PATENT DOCUMENTS

| | | | | | |
|---|---|---|---|---|---|
| 4,155,362 | A | * | 5/1979 | Jess ................... | A61M 5/14228 128/DIG. 12 |
| 4,857,056 | A | * | 8/1989 | Talonn ................ | A61M 5/1454 604/135 |
| 5,814,015 | A | * | 9/1998 | Gargano ............. | A61M 5/1456 604/67 |

(Continued)

FOREIGN PATENT DOCUMENTS

| EP | 1920793 A1 | 5/2005 |
|---|---|---|
| WO | 03/103763 A1 | 12/2003 |

(Continued)

OTHER PUBLICATIONS

"The Spring (TM) Technology: Motor-Based Pump vs. Spring-Based Pump", www.SpringNow.com, 2011 (c), a D-Medical Company.

(Continued)

*Primary Examiner* — Jenna Zhang
(74) *Attorney, Agent, or Firm* — Woodard, Emhardt, Henry, Reeves & Wagner, LLP

(57) ABSTRACT

A device for the dosed dispensing of a medium (e.g., therapeutic and/or diagnostic agent) for an insulin pump is proposed. The device comprises a transporting and transferring container, a measuring element, and an adjusting element for influencing a dispensing of the medium by way of a connection to an interior space. The transporting and transferring container has a reservoir for receiving the medium. The reservoir is closed by a displaceable element. The displaceable element is movably mounted in relation to (Continued)

the reservoir. A relative positioning of the displaceable element in relation to the reservoir determines the interior space of the reservoir available for receiving the medium. The measuring element senses the relative positioning of the displaceable element in relation to the reservoir. The measuring element and the adjusting element interact so that the dispensing of the medium is influenced by the relative positioning sensed by the measuring element.

27 Claims, 6 Drawing Sheets

(56) References Cited

U.S. PATENT DOCUMENTS

| | | | | |
|---|---|---|---|---|
| 8,257,310 | B2* | 9/2012 | Donovan | A61B 17/8872 604/154 |
| 8,385,972 | B2* | 2/2013 | Bochenko et al. | 455/556.1 |
| 2003/0216683 | A1* | 11/2003 | Shekalim | A61M 5/1454 604/67 |
| 2005/0159708 | A1* | 7/2005 | Sidler | A61M 5/1452 604/132 |
| 2010/0204659 | A1* | 8/2010 | Bochenko | A61M 5/1454 604/232 |
| 2011/0166426 | A1* | 7/2011 | Haueter | G01N 33/49 600/300 |

FOREIGN PATENT DOCUMENTS

| | | |
|---|---|---|
| WO | 2004/105827 A2 | 12/2004 |
| WO | 2007/122621 A2 | 11/2007 |

OTHER PUBLICATIONS

Hsu et al., "Development of peristaltic antithrombogenic micropumps for n vitro and ex vivo blood transportation tests", Microsyst Technol; 2007; 14: pp. 31-41.

* cited by examiner

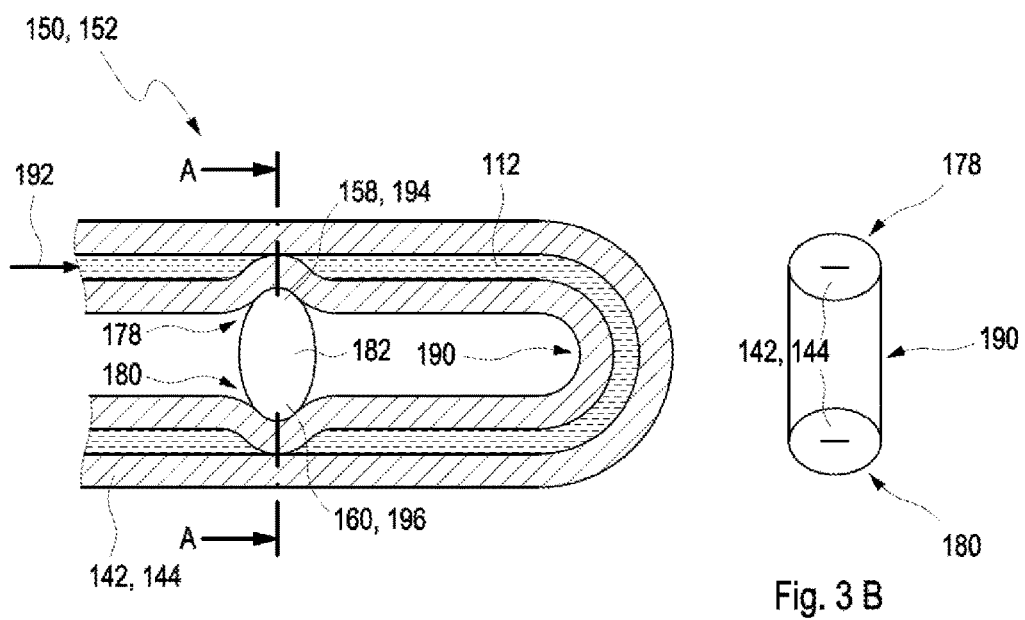
Fig. 3 A
Fig. 3 B
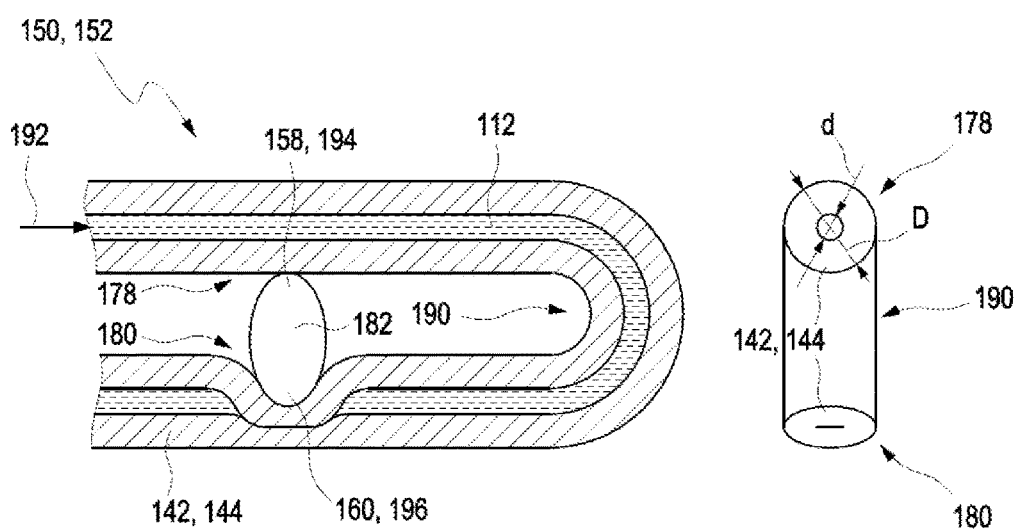
Fig. 3 C
Fig. 3 D

DEVICE FOR THE DOSED DISPENSING OF A FLUIDIC MEDIUM

CROSS-REFERENCE TO RELATED APPLICATIONS

This application is a continuation of EP 11170216.3, filed Jun. 16, 2011, which is hereby incorporated by reference.

BACKGROUND

The present disclosure generally relates to a device for the dosed dispensing of a fluidic medium and, in particular, relates to the dosed dispensing of a fluidic therapeutic and/or diagnostic agent, for example a dosed dispensing of insulin.

Such medication devices, methods and uses can be employed in many areas of the natural sciences, technology and medical engineering. One known device basically works on the principle of a reservoir for receiving a fluidic medium in which a plunger is mounted. This plunger may for example be electrically driven. Many insulin pumps that are on the market operate on this principle. Another known concept works with spring-mounted pressure accumulators, which can be manually filled by a user.

However, these known concepts present a number of technical challenges. For instance, with driven plungers, propulsion of the plunger is needed. This has the effect that pressure builds up in the fluidic medium and a fluid transfer takes place. In addition, this may involve hysteresis effects which may have an influence on the dosing accuracy. This technical challenge is made even more challenging by the fact that when dosing medicaments such as insulin for example, it is necessary to keep a highly accurate check on the dispensed amount in widely differing ranges. On the one hand, a highly accurate dosing is required at low dosage rates, in order for example to keep a check on a base load (basal rate). On the other hand, however, larger dosages must also be dispensed with high precision at short notice, in order to be able to ensure a peak load (bolus). If hysteresis effects or other static frictional effects occur, this may lead to considerable problems in terms of the dosing accuracy. A further challenge is that propulsion generally takes place by an electric drive, meaning that a correspondingly dimensioned power supply is required, for example a battery. This power supply has the effect that known medication devices generally have to be designed with a comparatively large volume.

A further technical challenge is that, before the device is put into operation, and virtually every time it is refilled, venting is generally required. For example, in a typical system, cartridges are exchanged, so venting (priming) of the entire fluidic system is generally required. Together with other technical challenges, this has the overall effect that a user generally has to perform many steps making the handling of the system much more difficult.

Therefore, there is a need to provide a device and method for the dosed dispensing of a fluidic medium which avoids the disadvantages of known devices and methods. In particular, there is a need to improve the ease of handling of the system, to reduce the volume and weight of the device and to increase the dosing accuracy especially for small dosages.

SUMMARY

According to the present disclosure, a device for the dosed dispensing of a medium (e.g., therapeutic and/or diagnostic agent) for an insulin pump is presented. The device comprises a transporting and transferring container, a measuring element, and an adjusting element for influencing a dispensing of the medium by way of a connection to an interior space. The transporting and transferring container has a reservoir for receiving the medium. The reservoir is closed by a displaceable element. The displaceable element is movably mounted in relation to the reservoir. A relative positioning of the displaceable element in relation to the reservoir determines the interior space of the reservoir available for receiving the medium. The measuring element senses the relative positioning of the displaceable element in relation to the reservoir. The measuring element and the adjusting element interact so that the dispensing of the medium is influenced by the relative positioning sensed by the measuring element.

Accordingly, it is a feature of the embodiments of the present disclosure to provide a device and method for the dosed dispensing of a fluidic medium that improves the ease of handling of the system, reduces the volume and weight of the device and increases the dosing accuracy especially for small dosages. Other features of the embodiments of the present disclosure will be apparent in light of the description of the disclosure embodied herein.

BRIEF DESCRIPTION OF THE SEVERAL VIEWS OF THE DRAWINGS

The following detailed description of specific embodiments of the present disclosure can be best understood when read in conjunction with the following drawings, where like structure is indicated with like reference numerals and in which.

DETAILED DESCRIPTION

Figure 1:
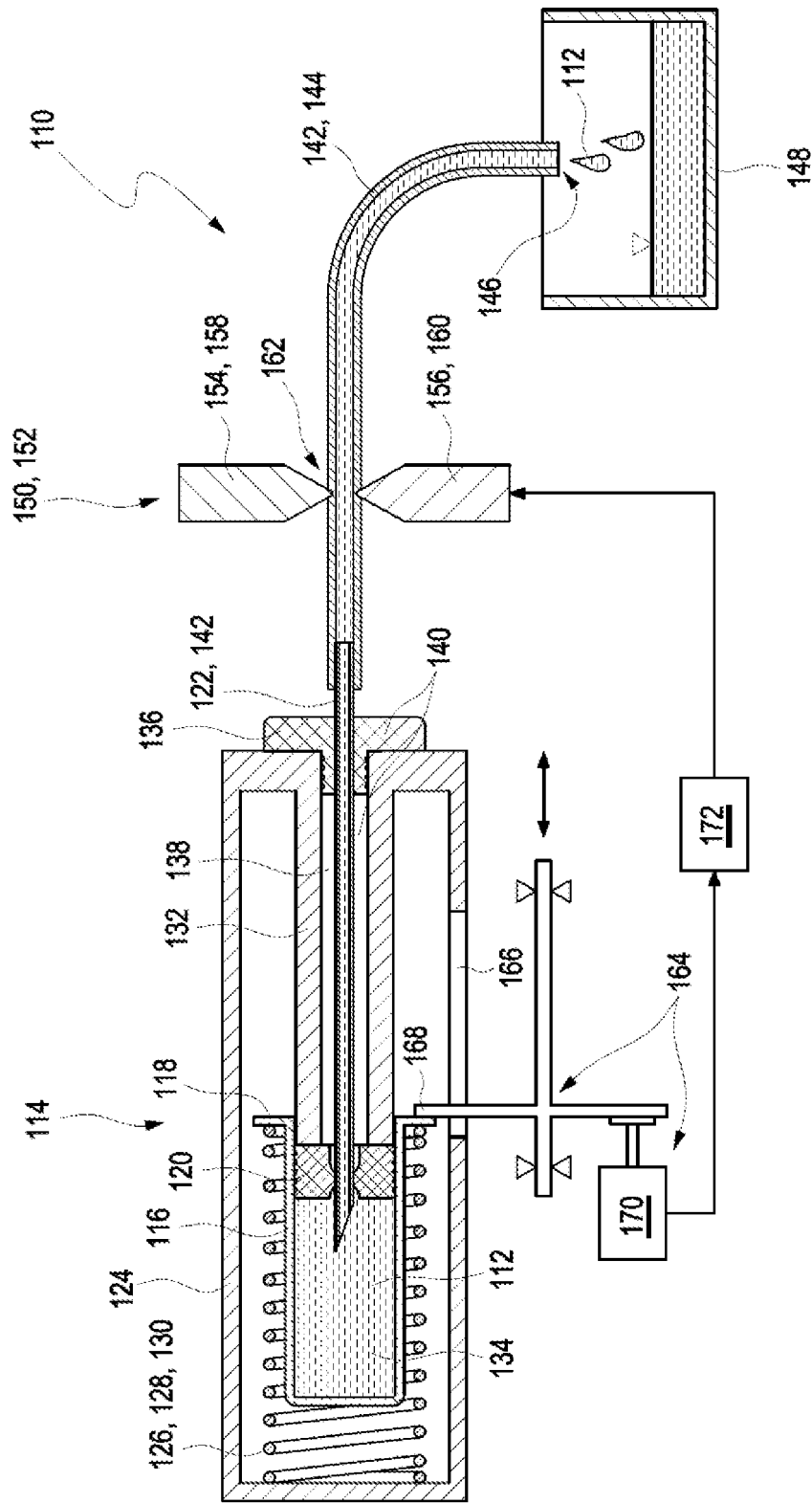
FIG. 1A illustrates a device according to an embodiment of the present disclosure.
FIG. 1B illustrates an enlarged representation of a transporting and transferring container for use in the device in FIG. 1A according to an embodiment of the present disclosure.
Figure 1:
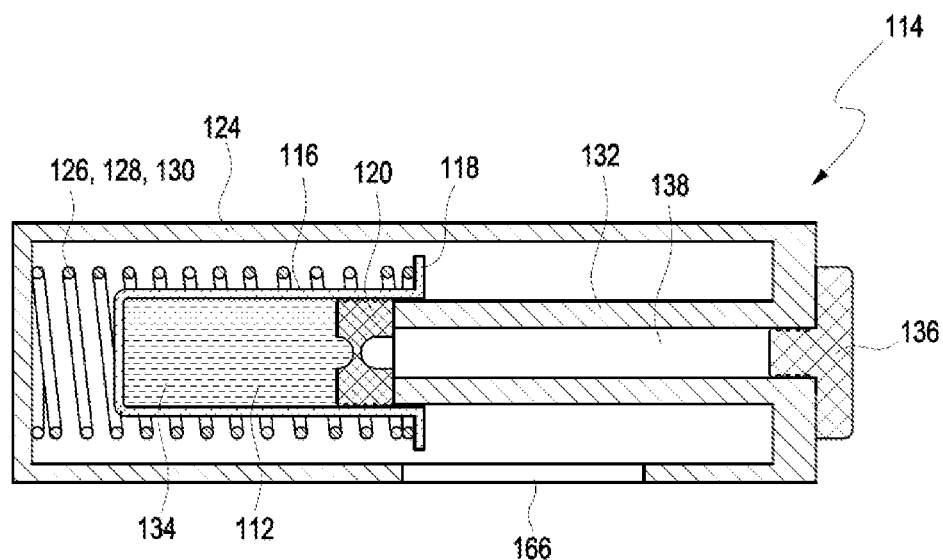

In the following detailed description of the embodiments, reference is made to the accompanying drawings that form a part hereof, and in which are shown by way of illustration, and not by way of limitation, specific embodiments in which the disclosure may be practiced. It is to be understood that other embodiments may be utilized and that logical, mechanical and electrical changes may be made without departing from the spirit and scope of the present disclosure.

A device for the dosed dispensing of a fluidic medium is presented. The device can be generally a device for dispensing a fluidic medium, i.e., a liquid and/or a gas, in a supervised manner, for example controlled by a corresponding program and/or controlled by a user.

A fluidic medium can generally means a liquid and/or a gas. A mixture of a number of liquids and/or gases may also be included. In one embodiment, the fluidic medium may comprise at least one fluidic diagnostic agent and/or at least one fluidic therapeutic agent. In an exemplary embodiment, the fluidic medium is insulin, so that, the device may be an insulin pump. However, the device may be configured in some other way and, apart from being configured for the dosed dispensing of at least one therapeutic and/or diagnostic agent, may also be configured for the dispensing of other types of fluidic media, in particular for use in the natural sciences and technology. For example, the device may also be used in the process control of chemical processes, for example in the case of a synthesis and/or an analysis.

A dosed dispensing of the fluidic medium can generally mean a dispensing of the fluidic medium in which a dispensed amount and/or a dispensing rate (for example specified in the form of a volume flow and/or in the form of a mass flow) corresponds at least to a prescribed requirement, this prescribed requirement can be of a static and/or variable.

The device can comprise at least one transporting and transferring container. A transporting and transferring container can generally mean a container for at least temporarily keeping the fluidic medium. In this transporting and transferring container, the fluidic medium may for example be stored and/or sold and/or temporarily kept. The transporting and transferring container can have at least one reservoir for receiving the fluidic medium. The reservoir can generally mean a device with at least one closed interior space, which can be sealed with respect to the fluidic medium, so that, in one embodiment, the fluidic medium can be kept in this interior space for a time period of at least a number of minutes. In another embodiment, the fluidic medium can be kept in this interior space for a time period of at least a number of hours. In another embodiment, the fluidic medium can be kept in this interior space for a time period of a number of days. In yet another embodiment, the fluidic medium can be kept in this interior space for a time period of at least a number of weeks, months or even years.

The reservoir can have at least one displaceable element. A displaceable element can generally mean an element which can be movably mounted in at least one dimension in relation to at least one further component part of the reservoir. This displaceable element may for example be linearly and displaceably mounted in at least one dimension in relation to a reservoir wall of the reservoir. For example, the displaceable element may comprise at least one stopper, which can be displaceably mounted in an interior space of the reservoir. However, other configurations can also be possible. The displaceable element may be accommodated completely in an interior space of the reservoir and for example be completely surrounded by a reservoir wall and/or may also for example completely or partially close off an interior space of the reservoir with respect to an exterior space and/or may be entirely or partially configured as a closure element of the reservoir.

For example, the reservoir may comprise at least one reservoir wall, which may for example be plastic and/or glass material. For example, the reservoir may be a tubular reservoir, the tubular reservoir can be closed at one end by the reservoir wall itself and closed, or able to be closed, at another end and/or in its interior by the displaceable element, for example the closure element. Alternatively or in addition to being closed by the displaceable element, the reservoir may also be entirely or partially closed by at least one closure element which is formed separately from the displaceable element, for example by a cap, for example a flanged cap, and/or a septum.

The displaceable element may for example be entirely or partially configured as a stopper, for example as a plastic stopper. In one embodiment, the displaceable element may be perforable so that at least one perforable element can be perforated in order to establish a fluid connection with the interior space of the reservoir. Alternatively or in addition, however, it is also possible for at least one perforable element which is formed separately from the displaceable element to be provided, for example at least one septum, which can be perforated in order to establish the fluid connection with the interior space of the reservoir.

The displaceable element can be movably mounted in relation to the reservoir. For example, the displaceable element may be linearly and displaceably mounted in relation to at least one reservoir wall of the reservoir, for example in that the displaceable element is movable and comprises a stopper which can be displaceably accommodated in the reservoir.

This movable mounting can be configured in such a way that a relative positioning of the displaceable element in relation to the reservoir can determine an interior space of the reservoir available for receiving the fluidic medium. For example, the interior space may be bounded by the reservoir wall of the reservoir and the displaceable element, in one embodiment, exclusively by these elements. For example, as long as it is kept in the interior space of the reservoir, the fluidic medium can only come into contact with the reservoir wall of the reservoir and the displaceable element, for example the displaceably mounted stopper.

The device can also comprise at least one measuring element, which can sense the relative positioning of the displaceable element in relation to the reservoir. A relative positioning of the displaceable element can generally mean a relative position and/or relative orientation between the displaceable element and the reservoir or at least a part of the reservoir other than the displaceable element, for example a reservoir wall, this relative position and/or relative orientation can be characteristic of or determinative for the dimensioning of the interior space of the reservoir available for receiving the fluidic medium. For instance, it may be an absolute position of the displaceable element in the reservoir, for example an absolute position of an interface between a stopper and the fluidic medium in the reservoir. However, other configurations are also possible, for example depending on the type of configuration of the displaceable element.

A measuring element can mean any desired device which can sense the relative positioning by at least one measuring method. In one embodiment, the measuring element may be designed to sense the relative positioning directly. Direct sensing of the relative positioning of the displaceable element in relation to the reservoir can mean a sensing in which an interface between the displaceable element and the fluidic medium is sensed in its positioning, for example in a system of coordinates in which the reservoir is situated. In particular, an absolute position and/or an absolute orientation in this system of coordinates may be sensed.

The device can also comprise at least one adjusting element for influencing a dispensing of the fluidic medium by way of at least one fluid connection to the interior space. A fluid connection can generally mean a device which comprises at least one fluidic conductor, by way of which the fluidic medium can be transferred from the interior space into an exterior space surrounding the reservoir directly or indirectly, or vice versa. In one embodiment, the fluid connection may comprise at least one hose connection, in particular at least one hose connection with at least one flexible hose. However, other configurations are also possible.

An adjusting element can generally mean an element which influences the dispensing of the fluidic medium that is to say for example optionally to make it possible and/or interrupt it and/or optionally to make it possible to differing degrees. At the same time, the adjusting element may be entirely or partially configured as a passive adjusting element, that is to say as an adjusting element which does not deliver the actual fluid transfer itself, but only influences it. Accordingly, the adjusting element may comprise at least one valve which does not itself drive the fluid transfer but merely influences it. For actually driving the transfer, the fluidic medium may for example be pressurized in the reservoir, for example by at least one energy unit, and/or at least one drive and/or at least one pump may be provided, in order to displace the fluidic medium out of the reservoir and/or suck it out of the reservoir, in order to deliver the dispensing of the fluidic medium. Alternatively or in addition, the adjusting element may, however, also itself be entirely or partially configured as an active adjusting element, in order to drive the transfer of the fluidic medium out of the interior space, that is to say the dispensing of the fluidic medium.

A dispensing of the fluidic medium can generally mean a process in which the fluidic medium is transferred out of the interior space. This dispensing may take place for example into an exterior space, which may be configured separately from the interior space, and/or into another device, for example into a vessel. Other configurations are also possible.

The measuring element and the adjusting element can interact in such a way that the dispensing of the fluidic medium can be influenced by the relative positioning sensed by the measuring element. Influencing of the dispensing of the fluidic medium can in this case be generally mean an operation in which the manner and means of the dispensing is dependent on the relative positioning sensed by the measuring element. For instance, the dispensing may be configured in such a way as to provide the existence of at least two different relative positions, which can be sensed by the measuring element and in which the dispensing of the fluidic medium is differently configured. The dispensing may differ in particular with regard to a dispensing rate and/or a dispensed amount. Generally, the dispensing may take place continuously, or discontinuously, so that for example a continuous mass flow and/or continuous volume flow can be influenced and/or that a discontinuous dispensing, for example a dispensing in pulses, can be influenced with regard to a total amount and/or with regard to a dispensing rate. In the case of discontinuous dispensing for example, an influencing of time periods of dispensing phases may take place and/or a ratio between dispensing phases and phases in which no dispensing of the fluidic medium takes place may be influenced.

The measuring element may generate at least one measuring signal corresponding to the relative positioning. The at least one measuring signal may for example be an electrical measuring signal and/or an optical measuring signal. A measuring signal generally means a signal which carries at least one item of information in a wire-bound or wireless manner. The measuring signal and/or the information may be of an analog or digital configuration. The measuring signal may comprise a machine-readable item of information concerning the relative positioning.

The device may have at least one controller. The controller can control the adjusting element in an open-loop and/or closed-loop mode by the measuring signal. For instance, the dispensing of the fluidic medium may generally be influenced automatically by the positioning sensed by the measuring element, for example by the controller. This controller may for example comprise electronics and/or a data processing device which is designed for open-loop and/or closed-loop control of the measuring signal. The open-loop controlling operation that can be carried out by the controller can generally mean an operation in which a variable to be controlled, for example by way of at least one adjusting element which generates at least one manipulated variable influencing a directly controlled member, is set to at least one reference variable. The closed-loop controlling operation, which can alternatively or additionally be carried out by the controller, can generally mean an operation in which an actual value of a controlled variable is sensed and in which, depending on a deviation of the actual value from a setpoint value, at least one corrective measure can be taken, for example in that at least one adjusting element can be used to generate a manipulated variable, which acts on a directly controlled member.

For instance, the device may be designed in particular in such a way that the adjusting element is controlled in an open-loop and/or closed-loop mode the measuring signal of the measuring element. For example, the device may be designed in such a way that at least a total amount of a dispensing of the fluidic medium and/or a dispensing rate of the fluidic medium is/are prescribed and used as a reference variable, which can be used as a reference variable for the open-loop control and/or as a setpoint value for the closed-loop control. The prescribed requirement may be provided by the device itself, may be provided by some other device, or may be provided for example by a user, for example in that the user prescribes this requirement by one or more input elements of the device. The device may influence to set or control in an open-loop and/or closed-loop mode, a dispensed absolute amount and/or a dispensing rate of the fluidic medium by the relative positioning sensed by the measuring element.

The measuring element may sense the relative positioning of the displaceable element in relation to the reservoir directly. The displaceable element may for example comprise a stopper which is displaceable in relation to the reservoir. The measuring element may for example sense a displacement of the stopper in the reservoir such as a linear displacement.

The measuring element may be designed in various ways, which can be realized individually or else in any desired combination. For instance, the measuring element may be selected from the group comprising a mechanical measuring element, a magnetic measuring element, an electronic measuring element, an inductive measuring element, a capacitive measuring element, a resistive measuring element, an optical measuring element, and an ultrasonic measuring element. Combinations of this group can also be used.

The measuring element may sense at least one position of at least one interface between the displaceable element and the fluidic medium. This may take place for example by a displacement between the displaceable element and the fluidic medium directly. In one embodiment, the measuring element may sense the relative positioning with an accuracy of at least 0.05 mm. In another embodiment, the accuracy can be of at least 0.01 mm.

The fluid connection may penetrate through the displaceable element such as, for example, the stopper. For example, the displaceable element may comprise a perforable stopper, such as, for example, a stopper comprised of plastic material and/or elastomer material. The fluid connection may for example comprise at least one cannula which can penetrate through the perforable stopper. However, configurations of the displaceable element other than a configuration as a perforable closure element are also possible.

Other embodiments regarding the movable mounting of the displaceable element in relation to the reservoir are possible. The device may have at least one housing. The housing can generally mean a device which protects the device outwardly from external mechanical influences. For example, the housing may be of a dimensionally stable configuration, that is to say none-deformable—at least under the effect of its own weight. The housing may for example be entirely or partially plastic or metal. The reservoir may be accommodated movably in the housing. The displaceable element may be fixed in relation to the housing, for example in that the displaceable element can be fixedly connected to the housing or can even form a component of the housing. However, an inverse configuration can also be possible, one in which the reservoir can be fixedly accommodated in the housing and the displaceable element can be movably mounted in the housing, or a combination in which both the reservoir and the displaceable element are mounted movably in relation to the housing.

In one exemplary embodiment, the reservoir can be movably accommodated in the housing, the displaceable element can be fixed in relation to the housing, and the measuring element can sense a relative positioning of the reservoir in the housing. This relative positioning of the reservoir in the housing can then in turn be used to deduce a relative positioning between the reservoir and the displaceable element since the displaceable element can be fixed in relation to the housing.

Various ways of configuring the fluidic medium can be possible. For instance, the fluidic medium can be sucked out of the interior space of the reservoir. Alternatively or in addition, the fluidic medium can be transported out of the interior space by being pressurized with a positive pressure. This positive pressure may for example be provided by mechanical or hydraulic and/or pneumatic pressurization. For example, the pressurization with the positive pressure may take place by the displaceable element being moved into the interior space and/or by the interior space of the reservoir which is available for receiving the fluidic medium being reduced in some way, by changing the relative positioning and/or relative orientation between the displaceable element and at least one further part of the reservoir, for example a reservoir wall.

The device may for example subject the displaceable element and/or the reservoir to a force in such a way that a positive pressure can be exerted on the fluidic medium and/or that the fluidic medium can be under an increased pressure, for example under a pressure increased with respect to the ambient pressure. In particular, the device may press the displaceable element against an abutment so that the displaceable element can be forced into the interior space. Forcing in can mean an operation in which a volume of the interior space is reduced by changing the positioning of the displaceable element in relation to the reservoir, irrespective of whether the reservoir and/or the displaceable element is/are then moved. The abutment may be for example a component of the housing. In one embodiment, the abutment can be entirely or partially a component of the transporting and transferring container, for example a reservoir housing of the transporting and transferring container, which does not necessarily have to be a component of the housing of the device and which can preferably be configured and handled independently of the housing of the device. For example, a reservoir housing of the transporting and transferring container which can have an abutment on which the displaceable element is seated may be provided, the reservoir of the transporting and transferring container being displaceable in relation to the abutment, so that the displaceable element is forced into the interior space by the abutment.

In order to press the displaceable element against the abutment, the device, in particular the transporting and transferring container may for example have at least one spring element. For example, this spring element may be a component of the transporting and transferring container. For instance, the transporting and transferring container may in particular have at least one reservoir housing, the reservoir being accommodated within the reservoir housing and, in addition, the at least one spring element being accommodated in the reservoir housing, so that for example the reservoir can be subjected to a force in such a way that the displaceable element can press against the abutment and can be forced into the interior space.

The fluid connection may take place through the abutment. For example, the abutment may be of a cylindrical configuration, for example as a hollow cylinder, a cannula for example of the fluid connection and/or a hose of the fluid connection extending through the abutment and, in one embodiment, also through the displaceable element.

The device may be configured in such a way that it can have at least one energy unit. The energy unit can subject the fluidic medium in the reservoir to a pressure. Consequently, an energy unit can generally mean a device that subjects the fluidic medium to the positive pressure. The energy unit may comprise at least one energy storage device and/or at least one actuator designed for the pressurization. The energy unit may have at least one spring element. The energy unit may have at least one energy storage device, such as for example a mechanical energy storage device or at least one spring element. In one embodiment, the energy unit may maintain the pressurization with the positive pressure for a time period of at least one month. In another embodiment, the energy unit may maintain pressurization for at least six months. In another embodiment, the energy unit may maintain pressurization for at least one year, or even for the entire storage lifetime or until the expiry of the shelf life of the device and/or of the transporting and transferring container, so that the positive pressure does not, for example, fall below 80% from an initial value within the stated time period.

The energy unit may be entirely or partially a component of the transporting and transferring container. The transporting and transferring container may for example have at least one reservoir housing, the reservoir being accommodated in the reservoir housing. The energy unit may be entirely or partially accommodated in an intermediate space between the reservoir housing and the reservoir, for example in an annular gap between the reservoir housing and the reservoir. The spring element may be mounted in this intermediate space, for example in the form of a helical compression spring or spiral spring.

The transporting and transferring container may be handled in a pressurized state, in which the fluidic medium in the reservoir is subjected to the positive pressure, independently of further components of the device. For example, the transporting and transferring container may be supplied already by the manufacturer in a pressurized state, in order then to be integrated for example in the device, so that, as far as the device is concerned, no further devices have to be required for the pressurization.

Other embodiments can have at least one adjusting element. For instance, the adjusting element may have at least one valve. This valve may be designed to influence a flow of the fluidic medium through the fluid connection. This influencing may take place in such a way that at least two different valve positions may be provided, positions in which a different flow of the fluidic medium through the fluid connection takes place, for example with different dispensed amounts and/or different dispensing rates. Alternatively or in addition, the valve may also be configured in such a way that a flow of the fluidic medium through the fluid connection can be optionally interrupted or allowed.

The fluid connection may have at least one hose connection. A hose connection can generally mean a device having at least one tubular, flexible and/or deformable element. For example, in one embodiment, the hose connection may have at least one plastic hose, elastomer hose or silicone hose.

The valve may have at least one valve element. This valve element may be designed to pinch the hose connection in at least one pinching region. This pinching may take place completely or else partially, so that during the pinching for example a flow of the fluidic medium through the pinching region can be restricted or completely interrupted. The at least one valve may have at least two valve elements. The at least two valve elements can be a components of one valve or can be components of different valves. Accordingly, the hose connection may be pinched by a single valve or by a number of valves. The pinching regions may be static and in a fixed positioning, but they may also be movably arranged, so that for example the pinching regions can also move in relation to the hose connection and for example can migrate. In this way, the valve may also for example entirely or partially perform a pumping function, for example a function of a peristaltic pump. Accordingly, the at least one adjusting element may also for example comprise a combination of at least one valve element and at least one pump, for example a peristaltic pump. The valve element may for example have at least one pinching element, for example an end of the valve element which can exert pressure on the hose connection, if appropriate in combination with at least one abutment, so that the hose connection can be pinched and deformed.

The hose connection may at least partially have a wall thickness which exceeds an inside diameter of the hose connection. This configuration can be advantageous since, in this way, for example at least one position of the at least one valve element in which the hose connection is already pinched, and in which a flow through the pinching region is prevented, can exist. Starting from this position, any further pinching may for example take place, pinching in which only a wall region of the hose connection is further pinched since the inside diameter has already been reduced to 0. This configuration can be advantageous if a valve has a number of valve elements which are mechanically coupled to one another, for example in the form of a valve rocker. A wall of the hose connection may accordingly serve as an extra allowance for surplus pinching and surplus deformation of the hose connection. The term inside diameter can generally be interpreted broadly. If the hose connection has a non-circular cross section, an inside diameter may generally be an equivalent diameter.

The valve may have at least two closed valve positions. A flow of the fluidic medium can be interrupted if the valve is in one of the closed valve positions. A valve position can generally mean a state of the valve. This state may relate to a single valve element which can assume at least two positions or it may relate to a number of valve elements which can assume different valve positions. The closed valve positions may be pinching positions. The fluid connection, a hose connection of the fluid connection, can be pinched in the pinching positions.

The closed valve positions may comprise end positions of a movement of a valve element of the valve. The valve element can be able for example to move between the valve positions.

The valve element may have a valve element which can be rotatably mounted about an axis and can interrupt the fluid connection by at least two pressure elements, for example opposite ends of the valve element, such as, for example, two pinching elements. For example, the valve element rotatably mounted about the axis may be a rocker, that is, the at least two pressure elements forming at least two portions arranged on different arms of the valve rocker, for example end portions.

The valve may be configured in such a way that, in a rest position, that is when no force is exerted on a valve element of the valve, it is in a closed valve position such that the flow of the fluidic medium through the fluid connection is interrupted. The fluid connection may have at least one hose connection. In the rest position, the valve element can pinch the hose connection in at least two pinching positions and thereby interrupting the fluid connection in the at least two pinching positions. Starting from this rest position, the valve element can for example move in two directions. The first pinching position can allow a flow of the fluidic medium and the second pinching position can have the effect of further pinching and consequently can maintain a closed state, or vice versa, depending on the direction.

The valve may have at least one valve element. This valve element may be able to be set in at least two static valve positions. A static valve position can mean a valve position in which the valve element stays during routine operation of the device. The valve may be configured in such a way that a flow of the fluidic medium through the fluid connection can be interrupted in all the static valve positions provided so that the valve may be in a fail-safe configuration. For example, at least two static valve positions may be provided, a hose connection being pinched in at least one pinching position in each of these static valve positions. For example, there may be provided a first static valve position, in which the hose connection is pinched in at least a first pinching position, and at least a second static valve position, in which the hose connection is pinched in at least a second pinching position, different from the first, so that in each case an interruption of the flow of the fluidic medium takes place either in the first pinching position or in the second pinching position. In this way, it can help ensure by the fail-safe feature that an overdosing of the fluidic medium never occurs, for example in that an unhindered flow of the fluidic medium through the valve takes place.

The valve may have at least two valve positions. In one embodiment, there can be at least two valve positions of the at least one valve element of the valve, for example at least two valve positions of the same valve element of the valve. The valve positions can be configured in such a way that the flow of the fluidic medium can be interrupted at at least one other point of the fluid connection.

The at least one adjusting element may be entirely or partially configured as a passive adjusting element, which can influence a flow of the fluidic medium without driving the actual transfer of the fluidic medium out of the reservoir, for example in the form of at least one valve. Alternatively or in addition, the at least one adjusting element may be entirely or partially configured as an active adjusting element, in order to drive the transfer of the fluidic medium. The latter configuration can be meaningful if the transporting and transferring container is not subjected to a positive pressure in a state of rest.

In an exemplary embodiment, the adjusting element may have at least one pump. This pump may be designed to suck the fluidic medium out of the interior space of the reservoir and/or to deliver the fluidic medium through the fluid connection and/or to dispense the fluidic medium in a supervised manner. This pump may be configured in various ways. In one embodiment, the pump can have at least one peristaltic pump or can be entirely or partially configured as a peristaltic pump. A peristaltic pump, in general, can mean a positive displacement pump in which the fluidic medium can be delivered by a mechanical deformation of the fluid connection or part of the fluid connection, such as a hose connection of this fluid connection. For this mechanical deformation, which may for example in turn comprise a pinching of the hose connection, the pump may for example have two, three or more actuators, which for example deform the fluid connection successively in a prescribed time sequence, for example pinch the hose connection successively in different positions. Such peristaltic pumps can be suitable for high-viscosity fluidic media.

In general, the device may for example be configured in such a way that the adjusting element comprises at least two actuators. The fluid connection can comprise at least one hose portion. The actuators can be designed to pinch the hose portion in at least two different pinching regions, for example staggered in terms of space and time. The at least two actuators may be configured independently of one another, but may also be electrically and/or mechanically connected to one another, so that for example a temporal and/or spatial pinching sequence may be prescribed by the connection. Between the actuators, there may be arranged in a stretchable region of the hose portion. The actuators may comprise at least one actuator on the inlet side and at least one actuator on the outlet side. The terms "inlet side" and "outlet side" relate to how the fluidic medium flows through the hose portion when the fluidic medium is dispensed from the medication device. The actuator on the inlet side is thus the one which is passed first in time by a volume element of the fluidic medium. The device may admit fluidic medium under pressure into the stretchable region between the actuators when the actuator on the inlet side is open and the actuator on the outlet side is closed. A "closed" actuator can mean a position of the actuator in which the respective actuator pinches the hose portion in the pinching region and prevents passage through this pinching region. With admission into the stretchable region, the stretchable region can be stretched. The device may also subsequently close the actuator on the inlet side and open the actuator on the outlet side, the stretchable region being relaxed and part of the fluidic medium flowing out of the stretchable region.

The device may have a modular structure and can have at least two modules, which can be connected to one another and, in one embodiment, can connect reversibly. For instance, the device may have at least one control module with at least one controller. The controller can control the actuating element in an open-loop and/or closed-loop mode by the measuring signal. A control module can generally mean any desired module which can undertake complete or partial control of the device. The transporting and transferring container may, on its own or with one or more components, form at least one further module of the device. The transporting and transferring container may be of an exchangeable configuration.

The device may also have at least one base module, with at least one baseplate, the control module and the transporting and transferring container being able to be connected directly or indirectly to the baseplate. The baseplate may for example be an element which has a planar or curved supporting surface, which can for example be applied directly or indirectly to a surface on the skin of a user.

The device may also comprise at least one fluidic module. This fluidic module may comprise at least part of the fluid connection. For example, the fluidic module may have at least one hose connection. The fluidic module may be disposable, so that, for example when the transporting and transferring container is changed; the fluidic module can also be exchanged.

The transporting and transferring container may be configured in such a way that the fluid connection can be established when the modules are connected. Establishing the fluid connection can mean a completion of the fluid connection in such a way that dispensing of the fluidic medium through the fluid connection from the interior space is made possible. This may take place by a perforation of the displaceable element.

A method for the dosed dispensing of a fluidic medium is presented. This method may take place using a device as described above. A fluidic therapeutic and/or diagnostic agent may be administered. The method may on the one hand be used for therapeutic and/or diagnostic purposes, for example on a human or animal body. Alternatively, however, the method may also be carried out in such a way that no therapeutic or diagnostic function is carried out on a human or animal body. For instance, the fluidic medium may for example be dispensed into another device, for example for an analysis or for the purpose of an in vitro diagnosis.

The reservoir may already be filled with the fluidic medium. Alternatively, the filling of the reservoir may also constitute part of the method. The filling of the reservoir may take place at the manufacturer. Alternatively, the reservoir may also be entirely or partially filled by a user, for example in the course of a process of using the device as intended. This filling may for example be performed through the displaceable element, for example by means of at least one syringe.

The device and method may have many advantages over known devices and known methods. For instance, a novel pump system, a medication pump, can be realized.

In one embodiment, the fluidic medium, for example the liquid for injection, can be kept permanently under a positive pressure. In this way, a positive pressure can be exerted on the fluidic medium, for example constantly, for example by means of the energy unit, for example an energy storage device and preferably a compression spring. As a result of increased gas solubility, a bubble-free system can be realized.

An advantage that may be possible is to dispense with fine-mechanical propulsion. The device may be configured without a plunger driven by a drive. Accordingly, no electrical power for such precision-mechanical propulsion has to be provided, as a result of which it is possible for example to dispense with an electrical energy storage device.

The device as a whole can be compact and have few components. For example, the device may comprise at least one transporting and transferring container which merely comprises two components, namely the reservoir and the displaceable element. For example, a displaceable and optionally penetrable stopper may be fixedly positioned as a displaceable element and a tube which is open at one end and is displaced in the housing when emptying the reservoir may be used as the reservoir.

An actual relative positioning of the displaceable element in relation to the reservoir may be sensed by the measuring element. For example, an actual displacement of the reservoir and/or of the displaceable element and/or of a plunger may be measured. This may take place for example by the measuring element. The measuring element may comprise one or more suitable sensors, which may for example be of a mechanical, optical or other configuration. By means of this at least one measuring element, it can be possible for example to sense an exact position of the displaceable element, for example of the displaceable stopper and/or of a plunger, in relation to the reservoir. Consequently, a customary open-loop control of propulsion may be replaced by a closed-loop control of the propulsion, since for example the sensed relative positioning (actual value) can be compared with at least one setpoint value. By contrast with conventional insulin pumps, in which there is an open-loop control of the propulsion, there can now be for example a closed-loop control of the propulsion. In this way, the dosing can be made more exact, since for example the fluidic medium can be under constant pressure and the displacement can for example serve as an exact measure of the dispensed amount of fluidic medium.

Furthermore, a relative displacement of the reservoir can be measured, for example within a housing of the device, which can be technically realized more easily than the measurement of a displacement of the displaceable element in the reservoir, for example as the measurement of the displacement of a stopper in the reservoir.

Furthermore, the influencing of the dispensing of the fluidic medium by the adjusting element can be realized in an easy and reliable way. For example, a valve control may undertake the dispensing of the fluidic medium, for example the dosing. For example, a simple open-close valve may be used, allowing a dispensed amount to be determined. Generally, for example, the measuring element may assume a closed-loop control function and/or be a component part of a closed-loop control circuit and/or map at least one control parameter. Considerably less energy is required for controlling a valve than for example for controlling propulsion. This can allow longer service lives of the device and/or smaller electrical energy storage devices, such as for example smaller batteries, to be realized.

Furthermore, the device may have a fail-safe configuration. For instance, the optional at least one valve may be designed for example in such a way that it goes over from one closed position into another closed position, so that a minimal flow can only occur when there is an active movement between the two closed positions, for example between the stop positions. In the event of a mechanical and/or electrical failure of components, uncontrolled flow can consequently be ruled out.

Another advantage can be to be able to dispense with venting (priming). For example, it can be possible to use a transporting and transferring container in which the fluidic medium is kept without any bubbles, for example by subjecting the same to a positive pressure. The use of bubble-free transporting and transferring containers means that there can be no risk of indeterminate air bubbles. Furthermore, the volume of the fluid connection, and optionally of an injection needle, is generally known. For instance, an injection needle may be a further component of the device. This volume of the fluid connection, for example of the injection hose, and optionally of the injection needle, can also be optimized and for example taken into account in the case of the first dose which is dispensed with the device. For instance it can be possible to dispense with active venting of the medication device by the user. A small injected volume of air, however, can be unproblematic, in the case of subcutaneous injection. It can be possible to dispense entirely with a preparatory step, and the risk of a potential malfunction, for example due to the injection of air or an incorrect amount of insulin, can be minimized or ruled out.

Furthermore, with the device, refilling and/or exchanging the fluidic medium, for example of the transporting and transferring container, can also be made easier. For example, the transporting and transferring container and/or the reservoir of the same can easily be exchanged for a full transporting and transferring container and/or a full reservoir. This exchange may take place in such a way that no air, or only a negligible amount of air, is introduced into the device. Here, too, it can be possible to dispense with priming.

Another advantage can be that the injection system can be divided into defined modules, which may in each case form a subassembly of their own. The transporting and transferring container, which may for example be pre-filled or which may be filled by a user, may serve for example as the first module. In the case of a pre-filled transporting and transferring container, an energy unit may be provided for example, with the task of subjecting it to positive pressure. The transporting and transferring container may for example provide a requirement for a prescribed time period, for example a daily requirement.

While the transporting and transferring container may preferably be entirely or partially configured as disposable, the optional control module may be configured as a reusable control unit, for example for controlling the adjusting element and for positioning the valve and optionally for data management. For example, the control module may ensure data management for a time period of 6-12 months. For example, the control module may comprise at least one data processing device and/or at least one data memory. Furthermore, the control module may comprise one or more operator control elements, for example one or more buttons and/or one or more other types of operator control elements. Furthermore, one or more other types of user interfaces may be prescribed, for example data interfaces, and/or one or more elements for a visual and/or acoustic and/or haptic output of data and/or information.

The device may be configured in such a way that the control module can be provided for many cycles of use, with many transporting and transferring containers, which can be directly or indirectly connected to the control module successively, for example in each case up until emptying. In this way it can be possible for example to realize in each case a disposable injection unit, with an infusion set and a fail-safe valve device, which may be designed for connection to the control unit and for the use of multiple pre-filled transporting and transferring containers, for example for a time period of 5-10 days. Furthermore, there can also be the possibility of using the proposed subassemblies to build up what is known as a patch pump, which can for example be applied directly or indirectly to a surface of the skin of a user.

Altogether, the overall size, weight and mechanics of the device can be greatly reduced in comparison with known devices. For instance, a modular structure, for example the structure with the proposed subassemblies, makes it possible in particular to construct devices, and medication pumps, with less reliance on mechanical parts, lower energy requirements and a lower weight in comparison with conventional devices. Since an exchange and/or re-filling of the transporting and transferring container can be realized considerably more advantageously, smaller transporting and transferring containers, for example with a daily requirement of at most 1 ml, can also be advantageous and, in turn, can allow a reduction in the overall size and weight. The use of a pre-filled transporting and transferring container can allow handling to be made very easy and safe, and it can generally additionally be possible to ensure bubble-free dispensing of the fluidic medium, for example bubble-free dispensing of insulin.

The filling of the device and/or of the transporting and transferring container may take place at the manufacturer's. Alternatively or in addition, the device and/or the transporting and transferring container can be filled manually by the user. Altogether, in this way for example a very user-friendly insulin pump can be realized, one in which more affordable disposable modules can be provided. Altogether, technical advantages with respect to sterility and good product stability can be obtained by the use of materials that are simple and known.

Further advantages can be obtained as a result of sensing the relative positioning of the displaceable element in relation to the reservoir by the measuring element. For instance, measuring of a dispensed volume of liquid from a pressurized reservoir can take place by measuring a longitudinal displacement of the reservoir. This direct measuring method generally does not have any hysteresis, or only slight hysteresis, and can consequently be more precise than known methods, in which motor revolutions are generally used as an indirect measure of the amount of the fluidic medium dispensed. The measurement of a relative positioning, for example a length measurement, does not necessitate the presence of a fluidic medium under pressure. For example, a conventional carpule can be used in conjunction with a micro pump, a plunger for example being drawn into the carpule and allowing itself to be used as a measure of a dispensed amount of liquid. For example, known containers that can be filled by the user, which are already in use today, may be used for this purpose. The at least one measuring element may therefore be generally configured for a length measurement. It can be possible by this length measurement for example to perform a closed-loop control of the adjusting element, for example a valve and/or a pump. The length measurement may take place for example by the transporting and transferring container having the form of a syringe and the length measurement taking place in the tube of the reservoir or through a reservoir wall. Alternatively or in addition, the transporting and transferring container may also merely have a perforable stopper, and the length measurement may take place for example from the outside.

If a transporting and transferring container in which the fluidic medium is liquid and is under a positive pressure is used, it can be possible for the formation of gas bubbles to be avoided, at least to a great extent. In particular, it can also be possible to dispense with a pump and/or to replace it with a valve.

A further advantage can be obtained from the possibility of configuring the adjusting element entirely or partially as a fail-safe valve. In the case of a fail-safe valve, it can be possible for example for a flexible and/or elastic dispensing hose of the fluid connection to be pinched, in particular for controlling a dispensed amount of liquid. A fail-safe configuration may ensure for example that a controller always moves from a closed position to a closed position and only dispenses liquid during the movement. Here, too, it can be advantageous to use elastic hoses with a large wall thickness and a small inside diameter, since with this design there is generally no stationary, non-dynamic position in which liquid can unwantedly escape.

The adjusting element may for example comprise at least two actuators and a stretchable region of a hose portion. In this way, a particularly simple principle for dispensing liquid can be realized. It can be possible for example with a closed actuator on the outlet side, for example with a closed output valve, for liquid to be introduced under pressure by way of an actuator on the inlet side, for example an open inlet valve, into the stretchable region, for example a flexible and/or elastic hose portion. In this way, the stretchable region, for example the hose can expand. With the actuator on the inlet side closed and the actuator on the outlet side open, the stretchable region can then relax, a small liquid aliquot being dispensed. The stretchable region is in this case not generally emptied completely, but the dispensed amount corresponds generally to the stretching of the stretchable region of the hose portion. It can thereby be possible to dispense extremely small amounts of liquid. It can be advantageous in this case to use elastic hoses with a great wall thickness and small inside diameter. This principle may for example correspond to a linear peristaltic pump, which for example uses two elements that can make use of an existing difference in pressure.

Referring initially to FIG. 1A, a first exemplary embodiment of a device 110 for the dosed dispensing of a fluidic medium 112 is shown in a sectional representation. The device 110 can comprise a transporting and transferring container 114, which in FIG. 1B is represented by way of example in a delivery state, likewise in a sectional representation. Reference is made hereafter to both figures together.

In one exemplary embodiment, the transporting and transferring container can comprise a reservoir 116, for example, comprised of glass or plastics. The reservoir 116 may, for example, as represented in FIGS. 1A and 1B, be a tube that can be closed at one end. The reservoir 116 may, for example, have a projecting peripheral rim 118 and may be closed by a displaceable element 120 movably mounted in the reservoir 116. For example, this displaceable element 120 may be a displaceable stopper. In one embodiment, the displaceable element 120 can be a perforable stopper. In FIG. 1B, which shows the transporting and transferring container 114 in the delivery state, the stopper has not yet been perforated. FIG. 1A shows the transporting and transferring container 114 accommodated in the device 110 and the displaceable element 120 perforated by a perforation element 122 such as, for example, a hollow needle and/or a cannula.

The reservoir 116 can be filled with the fluidic medium 112. The reservoir 116 can be accommodated in a reservoir housing 124, which may, for example, be entirely or partially transparent. The reservoir 116 itself may also be entirely or partially transparent, so that a user can for example visually check a filling level of the reservoir 116.

In an exemplary embodiment, the transporting and transferring container 114 can optionally comprises an energy unit 126, which can subject the fluidic medium 112 in the reservoir 116 to a pressure. For example, this pressurization may be integrated directly in a production process, so that the transporting and transferring container 114 can be delivered, for example, packaged, already in a state in which the fluidic medium 112 is subjected to a positive pressure. In an exemplary embodiment, the energy unit 126 can comprise an energy storage device 128 such as, for example, a mechanical energy storage device in the form of a spring element 130. This spring element 130 may, for example, as shown in FIGS. 1A and 1B, press the displaceable element 120 against an abutment 132, so that the displaceable element 120 is forced into an interior space 134 of the reservoir 116 and can consequently subject the fluidic medium 112 to the positive pressure. The abutment 132 may, for example, be a component of the reservoir housing 124 and/or other parts of the device 110. For example, the abutment 132 may be tubular. In FIG. 1B, the tubular abutment 132 can be closed by sealing 136. This sealing 136, which may for example be a stopper, may serve for example as sterile protection and can be removed before insertion of the transporting and transferring container 114 into the device 110, so that a clearance or a hollow space 138 of the abutment 132 can be exposed. In FIG. 1A, the perforation element 122 can in turn be inserted through this hollow space 138, for example, by a guide 140 and, for example, can bring about a centering of the perforation element 122. With this insertion, the perforation element 122 can perforate the displaceable element 120 and can establish a fluid connection with the interior space 134.

In one embodiment, the fluidic medium 112 may consequently be subjected to a positive pressure during transport and storage. This positive pressure may, for example, be maintained until use. In particular, the fluidic medium 112 may be kept in the reservoir 116 without bubbles. The fluidic medium may, for example, comprise a therapeutic and/or diagnostic agent, which may be kept in the reservoir 116 without bubbles. In one embodiment, the therapeutic and/or diagnostic agent can be insulin.

As soon as the perforation of the displaceable element 120 has taken place, as shown in FIG. 1A, the fluidic medium can be dispensed by way of a fluid connection 142. Apart from the optional perforation element 122, this fluid connection 142 may, for example, comprise at least one hose connection 144. This hose connection 144 may, for example, carry the fluidic medium 112 to a dispensing point 146, in which the fluidic medium 112 can be provided in a dosed manner. In the embodiment shown in FIG. 1A, it can be provided by way of example into a vessel 148. However, it can also be possible for the hose connection 144 to be connected to a further vessel directly or by way of one or more intermediate elements.

The device 110 can also comprise an adjusting element 150 for influencing a dispensing of the fluidic medium by way of the fluid connection 142. This adjusting element may for example, as shown in FIG. 1A, comprise a valve 152. In an exemplary embodiment, the valve 152 can comprise, by way of example, two valve elements 154, 156, which may act as actuators 158, 160 and which, as pinching elements, can pinch the hose connection 144 in at least one pinching region 162. One or both of the actuators 158, 160 may be movably mounted. The actuators 158, 160 may, for example, be movably mounted by a drive (not shown). The actuators 158, 160 can act together as a hose pinch and can influence, for example by allowing, restricting or interrupting, a flow of the fluidic medium 112 through the pinching region 162.

In an exemplary embodiment, the device 110 can also comprise at least one measuring element 164, which can sense a relative positioning of the displaceable element 120 in relation to the reservoir 116. This sensing can be based on a relative displacement of the reservoir 116 within the reservoir housing 124, in which the displaceable element 120 rests on account of the mounting on the abutment 132. For this purpose, the reservoir housing 124 can have a clearance 166. Through this clearance 166, a mechanical feeler 168 can reach into the interior of the reservoir housing 124 and can lie on the rim 118 of the reservoir 116. The feeler 168 can be used to transfer the position of the rim 118 to a measured-value transducer 170, which can for example convert the position of the rim 118 into an electrical signal. For example, the position may be converted by way of at least one resistor into a measured value and/or may be transformed by way of a capacitive or inductive coupling into a corresponding signal.

The measuring element 164 can be electrically connected to at least one controller 172. For this purpose, the controller 172 and the measuring element 164 may be configured as separate elements. Alternatively, however, the controller 172 may also be entirely or partially integrated in the measuring element 164 and/or the measuring element 164 may be entirely or partially a component of the controller 172.

The controller 172 can interact with the measuring element 164 and the adjusting element 150 in such a way that the dispensing of the fluidic medium 112 can be influenced by the relative positioning of the displaceable element 120 in relation to the reservoir 116 sensed by the measuring element 164. For this purpose, the controller 172 may, for example, control the adjusting element 150 in an open-loop and/or closed-loop mode. This open-loop and/or closed-loop control may generally be configured in various ways, which can also be combined in this or else in other exemplary embodiments. For example, the controller 172 may set a total discharged amount of the fluidic medium 112. For example, the controller 172 may generally initially allow a flow of the fluidic medium 112 through the valve 152, until a prescribed dispensed amount is reached. Subsequently, the flow may be interrupted by way of the valve 152. Alternatively or in addition, however, a rate of the dispensing of the fluidic medium 112 may be set, for example a rate in the form of a dispensed volume and/or in the form of a dispensed mass per unit of time. Various configurations are possible.

The device 110 in FIG. 1A can represent an example of a device 110 which is extremely easy to realize, of low cost and can be implemented with little installation space. In particular, the structural design of the transporting and transferring container 114 can easily make measuring the position of the displaceable element 120 possible. For example, with known insulin pumps, in many cases the inner stopper is displaced, but the position thereof would be considerably more difficult to sense than the sensing of the relative positioning of the reservoir 116 within the reservoir housing 124.

The simple hose pinch for flow control, by way of example, can also have numerous advantages over known flow controllers. In particular, a silicone hose can be used as the hose connection 144. Furthermore, the simple hose pinch can also generally be unproblematic with regard to insulin stability.

Special design features may also make a double pinch fail-safe, as will be explained in more detail below. This may mean for example that flow can only be possible in an oscillating operating mode of the adjusting element 150. Each end position and also a de-energized intermediate position block the flow. Alternatively or in addition, a hose pump can also ensure safe operation.

An exemplary embodiment according to FIG. 1A can also be configured extremely favorably in terms of installation space. To optimize and/or reduce the installation space, the component represented in FIG. 1A can be made flatter by laterally arranged springs. The thickness of the subassembly can then be generally only determined by the outside diameter of the reservoir 116 and/or of the transporting and transferring container 114.

Figure 2:
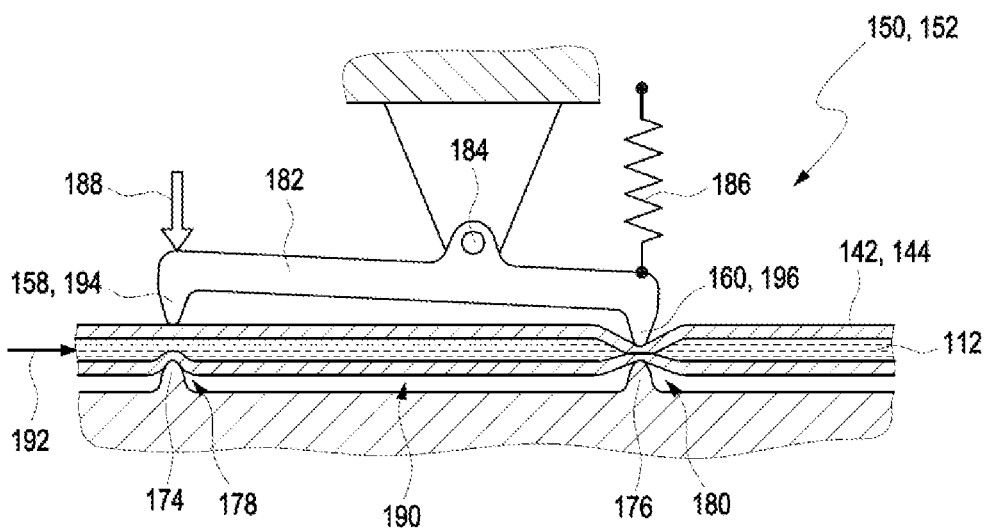
FIG. 2 illustrates a detailed representation of an alternative adjusting element for use in a device according to an embodiment of the present disclosure.

FIG. 2 is a further exemplary embodiment of an adjusting element 150, which may be used in a device 110, for example, according to FIG. 1A, or as an alternative or in addition to the adjusting element 150 represented in FIG. 1A. In one exemplary embodiment, the adjusting element 150 can have by way of example two actuators 158, 160, which can, in interaction with corresponding abutments 174, 176 for example, pinch the hose connection 144 in two spaced-apart pinching regions 178, 180. The actuators 158, 160 can in this way be actuated independently of one another or, as represented in FIG. 2, can be mechanically connected to one another, for example by way of a valve element 182, which in FIG. 2 can be a rocker and can be rotatably mounted about an axis 184. The valve element 182 may for example be activated by a spring element 186 and a valve drive 188, for example in such a way that the valve drive 188 can work against a spring force of the spring element 186 and in this way the valve element 182 can be turned optionally clockwise or anticlockwise about the axis 184.

Between the two actuators 158, 160 there may be arranged a hose portion 190 of the hose connection 144 that may be of a stretchable configuration. When the fluidic medium 112 flows out from the reservoir 116 through the hose connection 144, it can pass the hose portion 190 for example in a direction of flow 192, the actuator 158 first being passed as the actuator on the inlet side 194 and then the actuator 160 being passed as the actuator on the outlet side 196.

The adjusting element 150 may generally be a fail-safe configuration. For example, the adjusting element 150 may be configured in such a way that a flow through the hose portion 190 cannot be made possible in any rest position of the valve element 182. For example, the positioning of the adjusting element 150 may take place in such a way that, in a rest position or position of equilibrium, the actuator on the inlet side 194 and the actuator on the outlet side 196 equally block flow. Furthermore, the actuators 194, 196 may be configured in such a way that flow can only be possible through one of these actuators, but not through both of these actuators 194, 196 at the same time. This may take place for example in that, in the aforementioned rest position, both actuators 194, 196 pinch in the pinching regions 178 and 180. In a first open position, for example, the actuator on the inlet side 194 can then be moved upwards in FIG. 2, and the flow through this actuator can be allowed. However, the rigid mechanical connection between the actuators 194, 196 means that the actuator on the outlet side 196 can thereby be moved downwards and the hose connection 144 can be pinched still further in the pinching region 180. The wall region of the hose connection 144 thereby can act as an extra allowance, which can absorb additional pinching even though the actuator on the outlet side 196 was already previously in a closed position.

In this first position, fluidic medium 112 can flow through the actuator on the inlet side 194 into the hose portion 190, for example as a result of the positive pressure in the reservoir 116. The positive pressure of the fluidic medium 112 can have the effect that this hose portion 190, which is stretchable, is stretched. This first position or valve position of the adjusting element 150 is represented in FIG. 2.

Subsequently, the valve element 182 can be turned anticlockwise about the axis 184. The actuator on the inlet side 194 thereby can move downwards in FIG. 2 and, interacting with the abutment 174, can bring about closing this actuator on the inlet side 194. At the same time, the actuator on the outlet side 196 can move upwards in FIG. 2 and opened. The positive pressure prevailing in the hose portion 190, which can additionally be supported by restoring forces of the wall material of the hose connection 144, can cause part of the fluidic medium contained in the hose portion 190 to flow out through the actuator on the outlet side 196. Consequently, together with the actuators 194, 196, the hose portion 190 can act as a pumping system with a minimal flow rate.

As stated above, the adjusting element 150 may also be configured in such a way that there can be no state in which both actuators 194, 196 are open so that an unhindered flow or any flow at all can take place. Therefore, the adjusting element 150 can be a fail-safe configuration so that, for example, in the event of a failure of components of the adjusting element 150 and/or of the device 110, unhindered flow of the fluidic medium 112 cannot occur. For example, in a rest state the valve 152 may be configured in such a way that both actuators 194, 196 are closed.

FIGS. 3A-3F is another exemplary embodiment of an adjusting element 150 of a valve 152, which can act in a way analogous to the exemplary embodiment according to FIG. 2. Accordingly, with respect to possible configurations, reference can be made to the above description of FIG. 2. The adjusting element 150 can have a valve 152 with a valve element 182, whose ends act as actuators 158 and 160, respectively. The hose connection 144 can be taken in a loop around this valve element 182, so that the hose connection 144 can pass the valve element 182 twice, to be specific at two pinching regions 178 and 180. A direction of flow 192 of the fluidic medium 112 through a hose portion 190, which can be stretchable, between the actuators 158, 160 can serve to define the upper of these actuators 158,160 as the actuator on the inlet side 194, and the lower one in each case of these actuators 158, 160 as the actuator on the outlet side 196.

Figure 3:
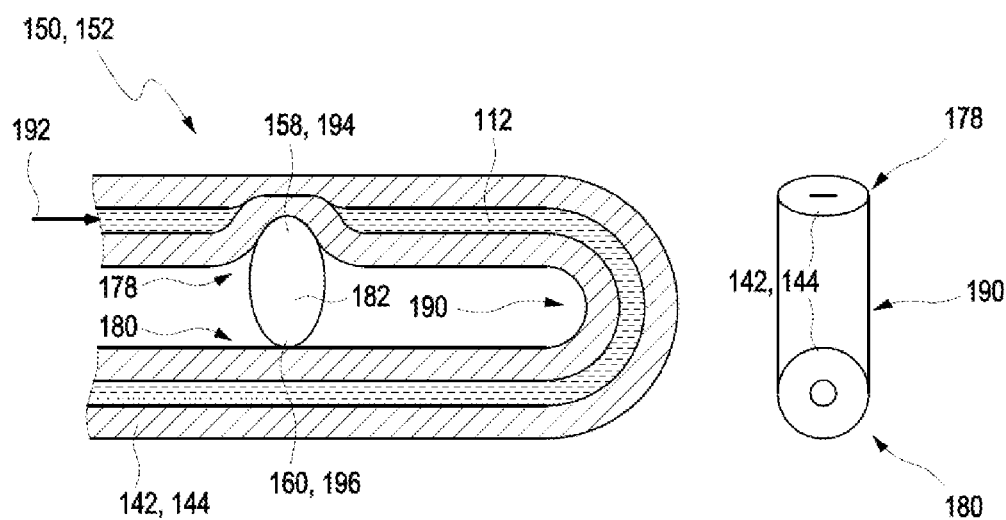
FIGS. 3A-F illustrate various representations of an adjusting element for use in a device according to an embodiment of the present disclosure.

In this respect, three different valve positions of the valve element 182 are represented in FIGS. 3A-3F. The valve element 182 can move vertically upwards and downwards, that is to say in each case perpendicularly in relation to the hose connection 144. FIGS. 3A and 3B show a first position, which may also be referred to as the rest position or the neutral position and in which the valve element 182 has not been deflected either upwards or downwards. FIGS. 3C-3D illustrate a first position, analogous to the position represented in FIG. 2, in which the actuator on the inlet side 194 is open and the actuator on the outlet side 196 is closed, in that the valve element 182 has been deflected downwards in FIG. 3C. This deflection may for example in turn take place by a valve drive 188, possibly in interaction with one or more spring elements 186, the optional at least one valve drive 188 and the optional at least one spring element 186 are not being represented in FIGS. 3A-3F. In FIGS. 3E-3F, on the other hand, a position in which the valve element 182 has been deflected upwards, so that the actuator on the inlet side 194 is closed and the actuator on the outlet side 196 is open, is shown. In general, FIGS. 3A, 3C and 3E respectively show the positions in a cross-sectional representation through the hose connection 144 from the side. FIGS. 3B, 3D and 3F show a sectional representation perpendicularly in relation to the hose connection 144 along the sectional line A-A in FIG. 3A. The valve element 182 is not shown in these sectional representations.

As stated above, the valve 152 may be a fail-safe configuration so that a complete flow through the valve 152 is not possible in any of the positions represented in which the valve element 182 can rest. For instance, in the neutral position represented in FIG. 3A, both valves 194, 196 are closed. In the first position, represented in FIG. 3C, the valve on the inlet side 194 is open, but the valve on the outlet side 196 is closed. In the second position, represented in FIG. 3E, the valve on the inlet side 194 is closed, whereas the valve on the outlet side 196 is open. As can be seen from FIGS. 3B, 3D and 3F, this may take place for example by both pinching regions 178, 180 being pinched in the neutral position shown in FIG. 3A (see section in FIG. 3B). When the valve element 182 is deflected into the position represented in FIG. 3C, the second pinching region 180 can be pinched further, whereas the first pinching region 178 is relieved and the flow is made possible there, as shown in FIG. 3D. In the case of the second position, FIG. 3F, on the other hand, starting from the neutral position, the first pinching region 178 is pinched further, whereas the second pinching region 180 is relieved and the flow is made possible there. In order to make further pinching of one of the two pinching regions 178, 180 possible from the already pinched neutral position in FIG. 3B, it can be particularly advantageous to make a wall material of the hose portion 190 stretchable. To be able to provide a stretching reserve, it can be additionally advantageous to make an inside diameter d (see FIG. 3D) of the hose portion 190 less than a wall thickness d of the hose portion 190.

With respect to the way in which the adjusting element 150 functions, reference can be made to FIG. 2. For instance, initially with the actuator on the outlet side 196 closed, the fluidic medium 112 can flow under pressure into the hose portion 190 through the open actuator on the inlet side 194. Subsequently, the actuator 194 on the inlet side may be closed and the actuator on the outlet side 196 may be opened, so that the fluidic medium, driven by the positive pressure, can flow out from the hose portion 190 through the actuator on the outlet side 196. It can be in turn possible in this way to realize a fail-safe adjusting element in which both actuators 194, 196 are closed in the neutral position represented in FIG. 3A and in which complete flow of the fluidic medium through the adjusting element 150 cannot be made possible in any valve position, in particular not in any static valve position.

Figure 4:
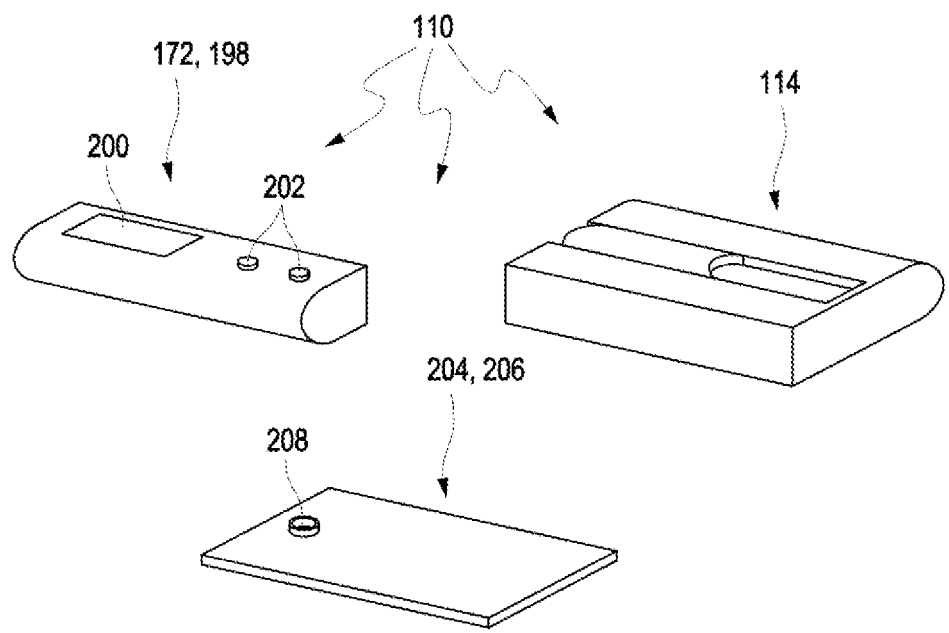
FIGS. 4A-B illustrate various views of the device put together in a modular manner according to an embodiment of the present disclosure.
Figure 4:
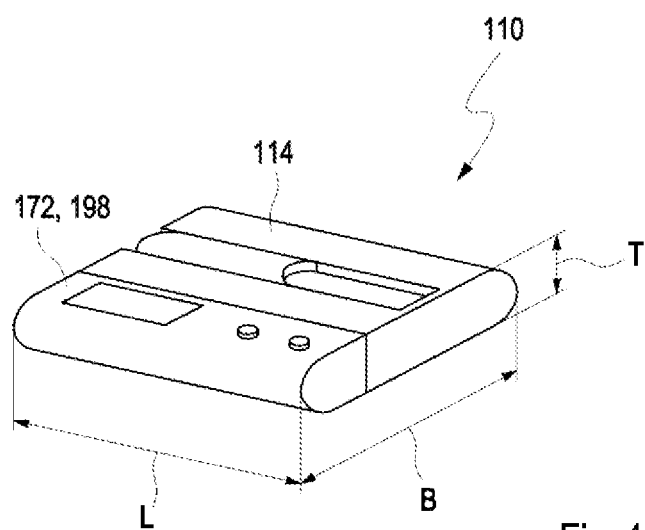

One particular advantage of the device 110 can be that the device 110 can have an especially small overall space and, in particular, can be made very flat. The elements of the transporting and transferring container 114 and of the controller 172 can be easily separable, which is conducive to the idea of a modular configuration. An example of a device 110 of a modular structure is represented in FIGS. 4A and 4B. FIG. 4A shows various modules of the device 110 in a separate representation, whereas FIG. 4B shows the device 110 in a state in which the modules have been put together.

For instance, the device 110 may initially comprise a transporting and transferring container 114. For example, the transporting and transferring container 114 may comprise a reservoir 116 and be configured in such a way that a fluidic medium 112 (not shown in FIGS. 4A and 4B) can be subjected to a positive pressure, for example by a manufacturer. Alternatively or in addition, there may also be provided at least one transporting and transferring container 114 in which the fluidic medium 112 can be kept under normal pressure or even under negative pressure. In this case, as stated in more detail below, the transfer of the fluidic medium 112 from the reservoir 116 may take place by means of at least one pump.

Apart from the transporting and transferring container 114, the first module of the modular device 110 in FIGS. 4A and 4B, the device 110 also comprises a control module 198. This control module 198 may for example comprise the controller 172, which for example can control a flow through a hose connection in an open-loop and/or closed-loop mode. The control module 198 may for example comprise one or more indicating elements 200, for example one or more displays, for example to indicate flow rates and/or dosage amounts. The control module 198 may for example also comprise one or more operator control elements 202, for example buttons, switches or similar operator control elements. The controller 172 may for example include one or more microprocessors and/or other types of data processing devices, which may for example be integrated in the control module 198. Alternatively or in addition, one or more electronic elements may also be provided, for example an electronic closed-loop control, for example to set a flow rate. As an alternative or in addition, the controller 172 may also comprise one or more switches, for example one or more end switches, the switching position of which may for example be variably settable, so that for example a specified total amount can be set.

The fluid connection 142 may likewise be entirely or partially included in the module of the transporting and transferring container 114 or be entirely or partially included in a separate module. The same also applies to the at least one adjusting element 150 (not shown in FIGS. 4A-B). For example, the device 110 may also comprise at least one fluidic module, which for example entirely or partially accommodates the fluid connection 142 and/or the adjusting element 150. The device 110 may also comprise a base module 204. This base module 204 is shown by way of example in FIG. 4A in the form of a baseplate 206, on which the control module 198 and the transporting and transferring container 114 can be mounted. The baseplate 204 may for example comprise an opening 208, through which the fluid connection 142 can be passed.

In FIG. 4B, the modular device 110 is shown in an assembled state. Altogether, the device 110 can have an extremely compact construction. For example, it may have a length L of about 55 mm, a width B of about 40 mm and a depth of about 15 mm. However, other dimensions are also possible. For example, the device 110 according to FIG. 4B may be designed to dispense about 1 ml.

The modular device 110 may be configured in such a way that for example the control module 198 can be reused. The other subassemblies, for example the base module 204 and/or the transporting and transferring container 114, may be disposable. The use of a pre-filled reservoir 116, for example a pre-filled insulin reservoir, can allow handling to be made very easy and safe, and bubble-free insulin dispensing can be ensured. Alternatively or in addition, the reservoir 116 can be filled manually by a user.

To prepare the device 110 for routine operation, for example, first an infusion set may be placed into the base module 204. Alternatively or in addition, the infusion set may also be entirely or partially a component of the base module 204. The infusion set may for example comprise the fluid connection 142 or parts of the same, for example a cannula for perforating the skin of a user. This infusion set may also for example comprise the hose connection 144 or parts of the same and/or the perforation element 122 or parts of the same and/or the adjusting element 150 or parts of the same. Alternatively or in addition, parts of the elements may also be arranged outside the infusion set, for example inside or outside the base module 204. For example, the baseplate 206 may have at least one plaster and/or at least one adhesive area, by which the baseplate 206 and/or the base module 204 can be entirely or partially adhesively attached to the user's skin. For example, the baseplate 206 together with the infusion set and/or parts of the same, for example the cannula for perforating the user's skin, may be adhesively attached onto the skin. During bathing or showering, the base module 204 may for example be dismantled. It may be possible for example for the baseplate 206 together with the cannula to remain on or in the skin, whereas for example the control module 198 and/or the transporting and transferring container 118 can be separated from the baseplate 206 and taken off. The baseplate 206 together with the infusion set may be exchanged at regular or irregular intervals, for example once a week.

The infusion set, for example, with the cannula for perforating the user's skin, may for example be entirely or partially a component of the baseplate 206 or be connected or able to be connected permanently or reversibly to the baseplate 206. It may be possible for example for a plug-in connection, a screw connection or a bayonet connection to be established between the infusion set and the baseplate 206. Other configurations are also possible.

The transporting and transferring container 114 may then be assembled, for example, by the perforation element 122 perforating the displaceable element 120. This perforation may for example take place automatically while the transporting and transferring container 114 is pushed into the base module 204. This may be followed for example by a functional test and an optional first venting, followed by an injection of the fluidic medium 112 into a body tissue, for example a subcutaneous insulin injection.

It can be particularly advantageous that, after emptying the reservoir 116, the transporting and transferring container 114 can be easily exchanged. After the exchange of the transporting and transferring container 114, the device 114 can be ready to operate again immediately, without further steps being required, such as venting for example. This is also suitable for a patch pump. This can for example comprise three or four subassemblies or modules. Since no motor and no great energy requirement may be necessary, it can be possible to optimize the size and weight of the device 110. In comparison with conventional pumps, such as for example insulin pumps, savings in volume and weight of about 25% can be possible.

The modules and their functions can be grouped in various ways. For example, an injection device can be integrated with the base module 204, for example the baseplate 206. The controller 172 can be integrated into the control module 198. Furthermore, other electronic components and the measuring element 164 can also be completely or partially integrated into the control module 198. Furthermore, the control module 198 may comprise one or more data processing devices. For example, in the control module 198 there may also be provided at least one data manager which may for example also comprise at least one database and/or at least one database program. The device 110 may for example also have at least one remote control device or interact with at least one remote control device, which is not represented in the figures and which may for example be connected to the controller 172, for example the control module 198, in a wireless or else wire-bound manner, so that for example a remote control function of the device 110 is possible. For example, a wireless connection in the form of a radio link or other connection by way of electromagnetic waves may be provided to a remote control device.

Furthermore, parts of the fluid connection 172 can also be entirely or partially integrated into the transporting and transferring container 114. In this way, the fluid connection 172 or parts of the same can be combined with the transporting and transferring container 114, for example to form a disposable system.

By combining the components in such a way, it is possible for example to establish a readiness for operation by the transporting and transferring container 114 first being connected to the control module 198. In a further step, for example the baseplate 206 can be fixed on the surface of a body. Furthermore, the transporting and transferring container 114 can be placed together with the control module 198 onto the baseplate 206, and operational readiness can be established.

In this way a user-friendly device 110 can be created, in particular a user-friendly insulin pump, in which affordable disposable subassemblies can replace the manual filling and priming (first filling). Technical advantages with respect to sterility and good product stability can be ensured by the use of materials that are simple and known. Furthermore, bubble-free changing of the reservoir can be ensured. The option of ensuring a fail-safe structural design of the adjusting element 150, in particular of the valve 152, allows the medication device to be configured with a high degree of safety and minimized risk for a user.

The device 110 represented in FIG. 1 can be modified in various ways. It can be possible for the modification to be carried out individually, in groups or as a whole. One possible configuration of modifications is represented in FIG. 5, in which an alternative device 110 is shown that is analogous to FIG. 1A.

Figure 5:
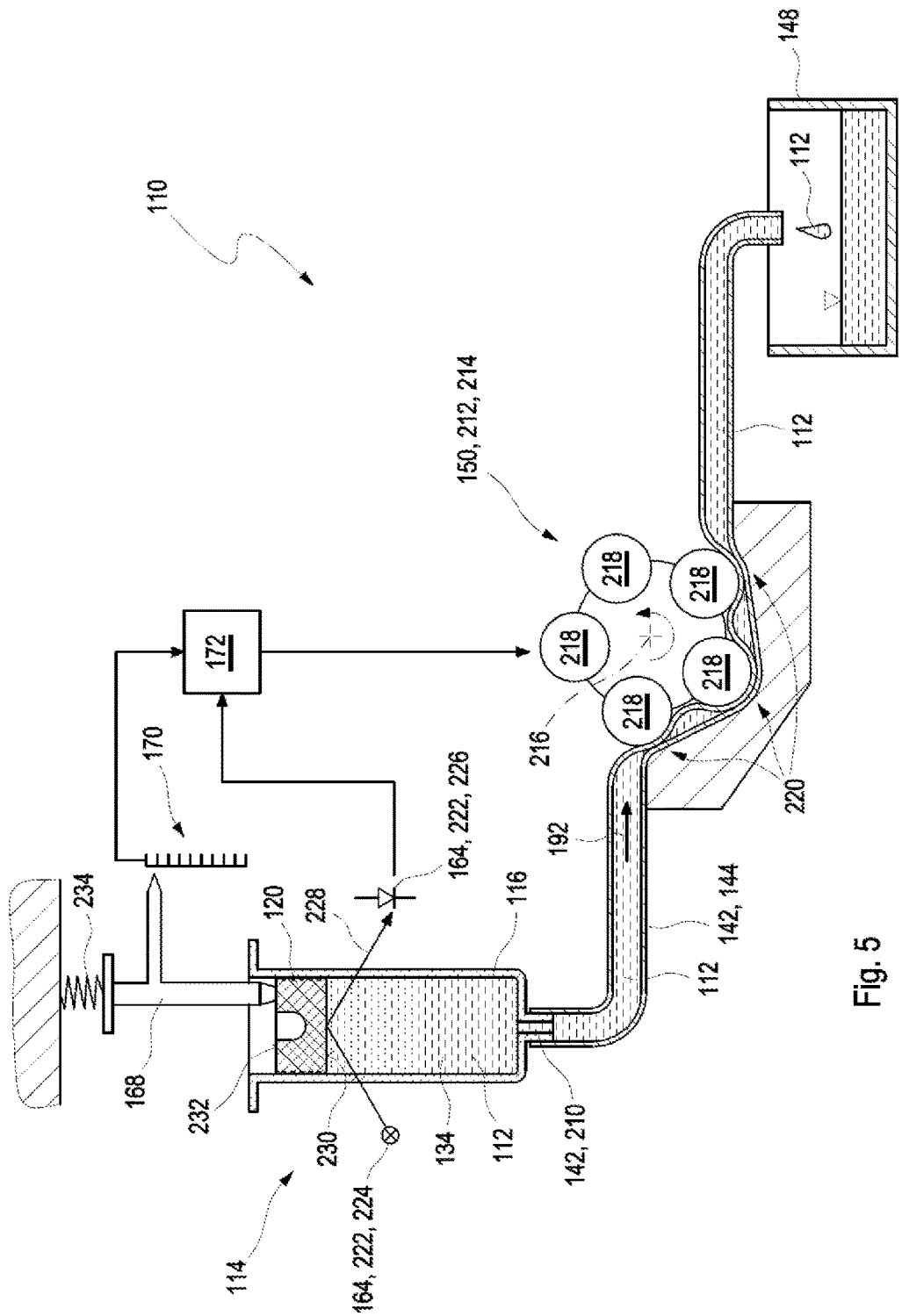
FIG. 5 illustrates a device with an adjusting element in the form of a pump according to an embodiment of the present disclosure.

For instance, the device 110 according to FIG. 5 first can comprise a transporting and transferring container 114 with a reservoir 116 for receiving a fluidic medium 112. This reservoir 116 can be closed by a displaceable element 120, for example by a stopper, the displaceable element 120 can be displaceably mounted in the reservoir 116. The establishing of a fluidic connection to an interior space 134 of the reservoir 116 may take place through the displaceable element 120. Alternatively or in addition, the reservoir 116 may also, as shown in FIG. 5, have a different type of fluid outlet, for example a connection piece 210, which may be a component of a fluid connection 142. In the exemplary embodiment according to FIG. 1A, this fluid connection may in turn comprise a hose connection 144, for example a silicone hose. The fluidic medium 112 in the reservoir 116 is not necessarily subjected to a positive pressure. To transfer the fluidic medium 112 out of the reservoir 116, it can be possible for example to use a suction force, which may for example be provided by one or more pumps 212. The pump 212 represented in FIG. 5 can represents an exemplary embodiment of an adjusting element 150, which can be used as an alternative or in addition to the valve 152 shown in FIG. 1A and by way of which the dispensing of the fluidic medium 112 can be influenced. In an exemplary embodiment, this pump 212 may for example be configured as a peristaltic pump 214, for example as a peristaltic pump 214 with actuators 218 rotating about an axis 216. These actuators 218 may for example act on the hose connection 144 in the migrating pinching regions 220, so that the fluidic medium 112 can be transported in a direction of flow 192 through the hose connection 144 and can be for example transported into a vessel 148.

Also represented in FIG. 5 is the case of transporting and transferring containers 114 without the fluidic medium 112 being subjected to positive pressure. In this configuration, by contrast with the sensing of the position of the movable reservoir 116 in the exemplary embodiment according to FIG. 1A, a position of the displaceable element 120 can be measured directly. Two options are shown. In one option, a measuring element 164 may be provided in the form of an optical measured-value transducer 222, with a light source 224 and a detector 226. For example, the reflection of a light beam 228 may in this case be used for directly sensing a position of an interface 230 between the displaceable element 120, for example the displaceable stopper, and the fluidic medium 112 in the interior space 134 of the reservoir 116. Alternatively or in addition, the position of the displaceable element 120 in relation to the reservoir 116 may also be sensed in some other way. For example, on a rear side 232 of the displaceable element 120, outside the interior space 134, there may be a feeler 168, which can be pressed against the rear side 232 for example by way of a spring element 234. The feeler 168 may for example be coupled to a measured-value transducer 170, so that in turn, as also in the case of the optical measured-value transducer 222, a signal to the controller 172 can be provided, by means of which for example the adjusting element 150 can in turn, irrespective of its configuration, be controlled in an open-loop and/or closed-loop mode.

To sum up, the following configurations are regarded as particularly advantageous.

Embodiment 1: A device for the dosed dispensing of a fluidic medium such as a fluidic therapeutic and/or diagnostic agent. In one embodiment, the device can be an insulin pump. The device comprises at least one transporting and transferring container, at least one measuring element, and at least one adjusting element for influencing a dispensing of the fluidic medium by way of at least one fluid connection to the interior space. The transporting and transferring container can have at least one reservoir for receiving the fluidic medium. The reservoir can have at least one displaceable element. The displaceable element can be displaceably mounted in relation to the reservoir and a relative positioning of the displaceable element in relation to the reservoir determining the interior space of the reservoir available for receiving the fluidic medium. The measuring element can sense the relative positioning of the displaceable element in relation to the reservoir. The measuring element and the adjusting element can interact in such a way that the dispensing of the fluidic medium is influenced by the relative positioning sensed by the measuring element.

Embodiment 2: The measuring element can be designed to generate at least one measuring signal corresponding to the relative positioning. The medication device can gave at least one controller. The controller can control the adjusting element in an open-loop and/or closed-loop mode by the measuring signal.

Embodiment 3: The device being can influence, in particular to set or to control in an open-loop and/or closed-loop mode, a dispensed absolute amount and/or a dispensing rate of the fluidic medium by the relative positioning sensed by the measuring element.

Embodiment 4: The measuring device can sense the relative positioning of the displaceable element in relation to the reservoir directly.

Embodiment 5: The displaceable element comprises a stopper which is displaceable in relation to the reservoir.

Embodiment 6: The measuring element can sense a displacement of the stopper in the reservoir, wherein the displacement can be a linear displacement.

Embodiment 7: The measuring element can be selected from the group comprising a mechanical measuring element, a magnetic measuring element, an electronic measuring element, an inductive measuring element, a capacitive measuring element, a resistive measuring element, an optical measuring element and an ultrasonic measuring element.

Embodiment 8: The measuring element can sense at least one position of at least one interface between the displaceable element and the fluidic medium.

Embodiment 9: The measuring element can sense the relative positioning with an accuracy of at least 0.05 mm. In another embodiment, the relative positioning can have an accuracy of at least 0.01 mm.

Embodiment 10: The fluid connection can penetrate through the displaceable element. In one embodiment, the displaceable element can be a stopper.

Embodiment 11: The displaceable element can comprise a perforable stopper. The fluid connection can comprise at least one cannula which penetrates the perforable stopper.

Embodiment 12: The device can have at least one housing. The reservoir can be movably accommodated in the housing and the displaceable element can be fixed in relation to the housing. The measuring element can sense a relative positioning of the reservoir in the housing.

Embodiment 13: The device can subject the displaceable element and/or the reservoir to a force in such a way that a positive pressure can be exerted on the fluidic medium and/or that the fluidic medium can be under increased pressure.

Embodiment 14: The device can press the displaceable element against an abutment so that the displaceable element can be forced into the interior space.

Embodiment 15: The fluid connection can take place through the abutment.

Embodiment 16: The device can have at least one energy unit. The energy unit can subject the fluidic medium in the reservoir to a positive pressure.

Embodiment 17: The energy unit can have at least one energy storage device. In one embodiment, the energy storage unit can be at least one mechanical energy storage device. In another embodiment, the energy storage unit can be at least one spring element.

Embodiment 18: The energy unit can maintain the pressure for a time period of at least one month in e one embodiment. In another embodiment, the energy unit can maintain the pressure for a time period of at least six months. In yet another embodiment, the energy unit can maintain the pressure for a time period of at least one year.

Embodiment 19: The energy unit can be a component of the transporting and transferring container.

Embodiment 20: It can be possible for the transporting and transferring container to be handled in a pressurized state independently of further components of the device.

Embodiment 21: The adjusting element can have at least one valve. The valve can influence, by optionally interrupting or allowing, a flow of the fluidic medium through the fluid connection.

Embodiment 22: The fluid connection can have at least one hose connection such as a flexible hose connection. The valve can have at least one valve element. The valve element can pinch the hose connection.

Embodiment 23: The hose connection can at least partially have a wall thickness which can exceed an inside diameter of the hose connection.

Embodiment 24: The valve can have at least two closed valve positions. A flow of the fluidic medium can be interrupted when the valve is in one of the closed valve positions.

Embodiment 25: The closed valve positions can be pinching positions. The fluid connection, in particular a hose connection of the fluid connection, can be pinched in the pinching positions.

Embodiment 26: The closed valve positions can comprise end positions of a movement of at least one valve element of the valve. The valve element can be able to move between the valve positions.

Embodiment 27: The valve element can comprise a valve element which can be rotatably mounted about an axis and can interrupt the fluid connection by at least two pressure elements such as by two pinching elements.

Embodiment 28: The valve in a rest position, in which no force is exerted on a valve element of the valve, can be in a closed valve position, in which the flow of the fluidic medium through the fluid connection can be interrupted.

Embodiment 29: The fluid connection can have at least one hose connection, in the rest position the valve element pinching the hose connection in at least two pinching positions and thereby interrupting the fluid connection in the at least two pinching positions.

Embodiment 30: The valve can have at least one valve element. The valve element can be set in at least two static valve positions. A flow of the fluidic medium through the fluid connection can be interrupted in all the static valve positions.

Embodiment 31: The valve can have at least two valve positions, such as at least two valve positions of at least one valve element of the valve. The valve positions can be respectively configured in such a way that the flow of the fluidic medium can be interrupted at at least one other point of the fluid connection.

Embodiment 32: The adjusting element can have at least one pump.

Embodiment 33: The pump can have a peristaltic pump.

Embodiment 34: The adjusting element can comprise at least two actuators. The fluid connection can comprise at least one hose portion. The actuators can pinch the hose portion in at least two different pinching regions.

Embodiment 35: A stretchable region of the hose portion can be arranged between the actuators.

Embodiment 36: The actuators can comprise an actuator on the inlet side and an actuator on the outlet side. The device can admit fluidic medium under pressure into the stretchable region between the actuators when the actuator on the inlet side is open and the actuator on the outlet side is closed. The stretchable region can be stretched. The device also can subsequently close the actuator on the inlet side and open the actuator on the outlet side. The stretchable region can relax and part of the fluidic medium can flow out of the stretchable region.

Embodiment 37: The device can be a modular structure. The device can comprise at least one control module with a controller. The transporting and transferring container can form at least one further module of the device. The transporting and transferring container can have an exchangeable configuration.

Embodiment 38: The device can also have at least one base module, with at least one baseplate. The control module and the transporting and transferring container can connect directly or indirectly to the baseplate.

Embodiment 39: The device can also have at least one fluidic module. The fluidic module can comprise at least part of the fluid connection.

Embodiment 40: The fluidic module can be disposable.

Embodiment 41: The transporting and transferring container can be configured in such a way that the fluid connection can be established when the modules are connected such as by a perforation of the displaceable element.

Embodiment 42: A method for the dosed dispensing of a fluidic medium such as fluidic therapeutic and/or diagnostic agent using a device, the method comprising using at least one transporting and transferring container. The transporting and transferring container can have at least one reservoir for receiving the fluidic medium. The reservoir can have at least one displaceable element that can be closed by at least one displaceable element in the form of at least one closure element. The displaceable element can be displaceably mounted in relation to the reservoir and a relative positioning of the displaceable element in relation to the reservoir determining an interior space of the reservoir available for receiving the fluidic medium. The relative positioning of the displaceable element in relation to the reservoir can be sensed by at least one measuring element. At least one adjusting element for influencing a dispensing of the fluidic medium by way of at least one fluid connection to the interior space can also be used. The measuring element and the adjusting element can interact in such a way that the dispensing of the fluidic medium can be influenced by the relative positioning sensed by the measuring element.

Embodiment 43: Use of a for dosing a therapeutic and/or diagnostic agent such as insulin.

It is noted that terms like "preferably," "commonly," and "typically" are not utilized herein to limit the scope of the claimed embodiments or to imply that certain features are critical, essential, or even important to the structure or function of the claimed embodiments. Rather, these terms are merely intended to highlight alternative or additional features that may or may not be utilized in a particular embodiment of the present disclosure.

Having described the present disclosure in detail and by reference to specific embodiments thereof, it will be apparent that modifications and variations are possible without departing from the scope of the disclosure defined in the appended claims. More specifically, although some aspects of the present disclosure are identified herein as preferred or particularly advantageous, it is contemplated that the present disclosure is not necessarily limited to these preferred aspects of the disclosure.

I claim:

1. A device for the dosed dispensing of a fluidic medium, the device comprising:
   a housing;
   at least one transporting and transferring container, wherein the at least one transporting and transferring container has at least one reservoir for receiving the fluidic medium, the at least one reservoir has at least one displaceable element, wherein the at least one reservoir is movably mounted in relation to the at least one displaceable element, and wherein a relative positioning of the at least one displaceable element in relation to the at least one reservoir determines an interior space of the at least one reservoir available for receiving the fluidic medium;
   at least one energy unit, wherein the at least one energy unit subjects the at least one reservoir to a force so that the fluidic medium is under increased pressure, wherein the energy unit is configured to move the at least one reservoir;
   at least one measuring element, wherein the at least one measuring element is configured to sense the relative positioning of the displaceable element in relation to the reservoir and configured to sense a relative positioning of the reservoir in the housing; and at least one adjusting element for influencing the dispensing of the fluidic medium by way of at least one fluid connection to the interior space;

wherein the at least one measuring element and the at least one adjusting element interact so that the dispensing of the fluidic medium is influenced by both of the relative positionings sensed by the at least one measuring element; and wherein the at least one reservoir is movably mounted in the housing and wherein the at least one displaceable element is fixedly coupled to the housing;

wherein the at least one reservoir is disposed inside the housing;

wherein the at least one displaceable element is secured at a fixed location relative to the housing;

wherein the at least one energy unit is configured to move the at least one reservoir relative to the housing;

wherein the at least one measuring element is configured to sense the position of the at least one reservoir relative to the housing;

wherein the at least one reservoir includes a rim; and wherein the at least one measuring element is configured to sense the position of the rim relative to the housing.

2. The device according to claim 1, wherein the fluidic medium is a fluidic therapeutic and/or diagnostic agent for an insulin pump.

3. The device according to claim 1, wherein the at least one measuring element generates at least one measuring signal corresponding to both of the relative positionings.

4. The device according to claim 3, further comprising, at least one controller, wherein the at least one controller controls the at least one adjusting element in an open-loop and/or closed-loop mode by the measuring signal.

5. The device according to claim 1, wherein the at least one displaceable element comprising a stopper, wherein the at least one reservoir is displaceable in relation to the stopper.

6. The device according to claim 5, wherein the at least one measuring element senses displacement of the stopper in the at least one reservoir.

7. The device according to claim 6, wherein the at least one displacement of the stopper in the at least one reservoir is a linear displacement.

8. The device according to claim 1, wherein the at least one measuring element senses at least one position relative to the at least one reservoir of at least one interface between the at least one displaceable element and the fluidic medium.

9. The device according to claim 1, wherein the at least one energy unit is a component of the at least one transporting and transferring container.

10. The device according to claim 1, wherein the at least one adjusting element has at least one valve, wherein the at least one valve influences a flow of the fluidic medium through the at least one fluid connection.

11. The device according to claim 10, wherein the at least one valve interrupts the flow of the fluidic medium through the at least one fluid connection.

12. The device according to claim 10, wherein the at least one valve allows the flow of the fluidic medium through the at least one fluid connection.

13. The device according to claim 10, wherein the at least one valve has at least two closed valve positions and wherein the flow of the fluidic medium is interrupted when the at least one valve is in one of the closed valve positions.

14. The device according to claim 13, wherein the at least two closed valve positions comprises end positions of a movement of at least one valve element of the at least one valve and wherein the at least one valve element is able to move between the at least two valve positions.

15. The device according to claim 10, wherein the at least one valve in a rest position, in which no force is exerted on a valve element of the at least one valve, and in a closed valve position, in which the flow of the fluidic medium through the at least one fluid connection is interrupted.

16. The device according to claim 10, wherein the at least one valve has at least two valve elements, wherein the at least two valve elements are able to be set in at least two static valve positions, and wherein a flow of the fluidic medium through the at least one fluid connection is interrupted in all the static valve positions.

17. The device according to claim 1, wherein the at least one adjusting element has at least one pump.

18. The device according to claim 1, wherein the at least one adjusting element comprises at least two actuators and the at least one fluid connection comprises at least one hose portion, wherein the at least two actuators pinch the at least one hose portion in at least two different pinching regions, wherein a stretchable region of the at least one hose portion is arranged between the at least two actuators, and wherein the at least two actuators comprise an actuator on the an inlet side and an actuator on the an outlet side.

19. The device according to claim 18, wherein the device admits fluidic medium under pressure into the stretchable region between the at least two actuators when the actuator on the inlet side is open and the actuator on the outlet side is closed, wherein the stretchable region is stretched.

20. The device according to claim 18, wherein the device subsequently closes the actuator on the inlet side and open the actuator on the outlet side, wherein the stretchable region is relaxed and part of the fluidic medium flows out of the stretchable region.

21. The device according to claim 1, wherein the device is modular and further comprising, at least one control module with a controller, wherein the at least one transporting and transferring container forms at least one module of the device and is exchangeable.

22. The device according to claim 1, wherein the at least one displaceable element has a septum to allow fluid communication between the interior space and the at least one fluid connection.

23. The device according to claim 1, wherein the device is configured to press the at least one displaceable element against an abutment, such that the at least one displaceable element is pressed into the at least one reservoir.

24. The device according to claim 23, wherein the at least one fluid connection takes place through the abutment.

25. The device according to claim 1, wherein the at least one fluid connection penetrates the at least one displaceable element.

26. The device according to claim 1, wherein the at least one energy unit is configured to subject the at least one reservoir to the force so that the fluidic medium is under the increased pressure independently of the housing of the device.

27. The device according to claim 1, wherein the housing defines a clearance through which the at least one measuring element senses the position of the rim.

* * * * *